United States Patent [19]

Anderson et al.

[11] 4,229,368
[45] Oct. 21, 1980

[54] ESTERS AND THIOLESTERS OF UNSATURATED ACIDS

[75] Inventors: Richard J. Anderson; Clive A. Henrick, both of Palo Alto, Calif.

[73] Assignee: Zoecon Corporation, Palo Alto, Calif.

[21] Appl. No.: 45,037

[22] Filed: Jun. 4, 1979

[51] Int. Cl.$^3$ .................... C07C 69/76; C07C 121/70; C07C 153/11

[52] U.S. Cl. .................... 260/465 D; 260/340.5 R; 260/455 R; 560/8; 560/9; 560/20; 560/21; 560/55; 560/59; 560/83; 560/85; 560/102; 560/104; 424/282; 424/301; 424/304; 424/308; 424/309

[58] Field of Search ........ 260/465 D, 455 R, 340.5 R; 560/104, 8, 9, 55

[56] References Cited

U.S. PATENT DOCUMENTS 4,161,535  7/1979  Meyer et al. ................ 260/465 D X

*Primary Examiner*—Dolph H. Torrence

[57] ABSTRACT

Esters and thiolesters of α-substituted unsaturated acids, intermediates therefor, synthesis thereof, and the use of said esters and thiolesters and compositions thereof for the control of pests.

18 Claims, No Drawings

ESTERS AND THIOLESTERS OF UNSATURATED ACIDS

This is a continuation-in-part of Ser. No. 902,624, filed May 4, 1978, abandoned, the entire disclosure of which is incorporated herein by reference.

This invention relates to novel esters and thiolesters of α-substituted unsaturated acids, novel intermediates therefor, synthesis thereof, and the control of pests.

The esters and thiolesters of the present invention are represented by the following formula (A):

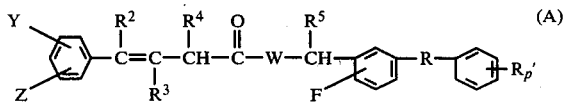

wherein:
R is oxygen, sulfur, methylene or carbonyl;
R' is hydrogen, fluoro, bromo, chloro, trifluoromethyl, methyl, methoxy or methylthio;
each of $R^2$ and $R^3$ is independently selected from hydrogen, chloro, fluoro, bromo, lower alkyl, lower alkenyl, lower alkoxy, cycloalkalkyl, and lower haloalkyl;
$R^4$ is lower alkyl of 2 to 5 carbon atoms, lower alkenyl of 2 to 5 carbon atoms, or cyano;
$R^5$ is hydrogen, cyano, ethynyl or methyl;
W is oxygen or sulfur;
t is zero, one, two, three or four;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio; and
Z is independently selected from the values of Y, cycloalkyl, and lower haloalkoxy; or
Y and Z form a methylenedioxy group.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of R through $R^5$, p, t, W, Y and Z is as defined hereinabove, unless otherwise specified.

The compounds of formula (A) can be synthesized as outlined below.

In the general practice of the above synthesis, an acid, salt thereof or the acid chloride is reacted with an alcohol of formula II to form the carboxylic ester A'. For example, an acid chloride of the acid of formula I is reacted with an alcohol of formula II in an organic solvent such as diethyl ether in the presence of triethylamine. In another embodiment, an acid of formula I and an alcohol of formula II are reacted in an organic solvent such as methylene chloride in the presence of 4-dimethylaminopyridine and dicyclohexylcarbodiimide to form an ester of formula A'. In another synthesis, the acid of formula I or salt thereof is reacted with the bromide, chloride or mesylate of the alcohol of formula II to form an ester of formula A'. The starting materials of formula I are described by Anderson and Henrick, Ser. No. 902,624 and Meyer et al, Offenlegungsschrift No. 27 43 425. The alcohols of formula II can be made as described by Fuchs et al, Offenlegungsschrift Nos. 27 09 264 and 27 39 854, and reference cited therein. The alcohols of formula II or the bromide thereof can be prepared also by reaction of a 3-bromofluorotoluene, e.g., 3-bromo-4-fluorotoluene and phenol or R' substituted phenol with sodium hydride, cuprous chloride, and pyridine using the procedure of A. L. Williams et al., J. Org. Chem. 32, 2501 (1967) to form a phenoxy substituted fluorotoluene, e.g., 4-fluoro-3-phenoxytoluene from the reaction of phenol and 3-bromo-4-fluorotoluene. By reaction of the phenoxyfluorotoluene intermediate with N-bromosuccinimide in the presence of benzoyl peroxide, the bromide is obtained, e.g., 4-fluoro-3-phenoxybenzyl bromide. The bromide can be converted to the corresponding aldehyde, e.g., 4-fluoro-3-phenoxybenzoldehyde, by treatment with sodium bicarbonate in dimethylsulfoxide using the method of Kornblum et al, J. Am. Chem. Soc. 79, 6562 (1957) or A. P. Johnson et al, J. Chem. Soc. 520 (1964). The aldehyde can be converted to the alcohol, e.g., 4-fluoro-3-phenoxybenzyl alcohol, by treatment with lithium aluminum hydride or the like. Compounds of formula II wherein $R^5$ in cyano can be prepared by reaction of the aldehyde with sodium bisulfite and sodium cyanide by conventional procedures. Compounds of formula II wherein $R^5$ is ethynyl or methyl can be prepared by Grignard reaction of the aldehyde.

The thiolesters of formula (A) can be prepared by the reaction of, for example, the sodium salt of a thioacid corresponding to formula I with the bromide or mesylate of the alcohol of formula II.

The following terms, wherever used in the description herein and the appended claims, have the meaning defined below, unless otherwise specified hereinafter.

The term "lower alkyl" refers to an alkyl group, straight or branched, having a chain length of one to eight carbon atoms. The term "lower haloalkyl" refers

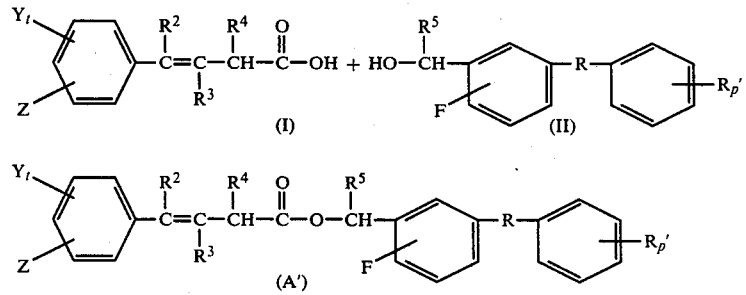

to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to eight carbon atoms. The term "lower alkylthio" refers to an alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve, such a cyclopropanemethyl, cyclobutaneethyl, cyclohexanemethyl, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight, more usually 0.01 to 25 percent.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithordoros.

The compounds of the present invention can be used in combination with other pesticides such as the carbamates, phosphates and insect growth regulators, e.g., propoxur, carbaryl, naled, dichlorvos, methoprene, kinoprene, hydroprene, cyhexatin resmethrin, permethrin and fenvalerate.

The following examples are provided to illustrate the practice of the present invention. Temperature is given in degrees Centigrade. RT means room temperature.

EXAMPLE 1

To 2.14 g (10 mmol) of 2-isopropyl-4-phenyl-3-pentenoic acid, 10 ml ether and 10 ml hexamethylphosphoric triamide (HMPT), under nitrogen, is added 1.45 g (10.5 mmol) potassium carbonate and (10.5 mmol) 4-fluoro-3-phenoxybenzyl bromide. The reaction is stirred about 16 hours and then poured into hexane and water. The organic phase is washed with water, saturated sodium chloride, and dried over calcium sulfate. Solvent is removed by rotoevaporation to yield the 4-fluoro-3-phenoxybenzyl ester of 2-isopropyl-4-phenyl-3-pentenoic acid, which can be further purified by preparatory thin layer chromatography (prep. TLC) eluting with ethyl acetate/hexane.

EXAMPLE 2

To a stirred solution of 4-fluoro-3-phenoxybenzyl alcohol (0.22 g, 0.99 mmol) and triethylamine (0.14 g, 1.38 mmol) in ether (about 15 ml), under nitrogen, is added by syringe a solution of the acid chloride of 4-(4-fluorophenyl)-2-isopropyl-3-butenoic acid (1.5 mmol) in ether. The mixture is stirred for 30 minutes and then quenched with saturated aqueous sodium bicarbonate. The ether phase is washed with aqueous sodium bicarbonate, water and brine and filtered through silica. Evaporation of solvent, followed by thin layer chromatography using a circular chromatograph, eluting with 20 percent ether/hexane, gives 4-fluoro-3-phenoxybenzyl 4-(4-fluorophenyl)-2-isopropyl-3-butenoate.

EXAMPLE 3

A. To a solution of 4-fluoro-3-phenoxybenzaldehyde (0.39 g, 1.8 mmol) in 25 ml of ether is added 25 ml of water followed by sodium cyanide (0.149 g, 3.04 mmol). The mixture is stirred vigorously while a solution of sodium bisulfite (0.257 g, 2.47 mmol) in 15 ml of water is added over about 5 minutes. The reaction mixture is stirred for two hours. The organic phase is separated, washed with water, dried over calcium sulfate and solvent evaporated to give α-cyano-4-fluoro-3-phenoxybenzyl alcohol.

B. To the acid chloride of 4-(4-fluorophenyl)-2-isopropyl-3-butenoic acid (2.5 mmol) in ether is added 1.3 ml of triethylamine followed by α-cyano-4-fluoro-3-phenoxybenzyl alcohol (2.4 mmol) in 5 ml of ether, from part A above, over about 2 minutes. The reaction mixture is stirred for about 18 hours and then quenched with saturated aqueous sodium bicarbonate. The organic phase is washed with aqueous sodium bicarbonate, water and brine, dried over calcium sulfate and solvent evaporated. The crude product is chromatographed on a circular chromatograph eluting with ether/hexane to give α-cyano-4-fluoro-3-phenoxybenzyl 4-(4-fluorophenyl)-2-isopropyl-3-butenote.

EXAMPLE 4

To a stirred solution of a-cyano-4-fluoro-3-phenoxybenzyl alcohol (437 mg, 1.8 mmol), 4-(4-chlorophenyl)-2-isopropyl-3-butenoic acid (2.0 mmol) and 4-dimethylaminopyridine (0.65 mmol) in 2 ml of methylene chloride and 2 ml of dimethylformamide is added N,N'-dicyclohexylcarbodiimide (2.0 mmol). The reaction mixture is stirred, under nitrogen, for two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated. The crude product is chromatographed on a rotary chromatograph eluting with 25 percent ether/hexane to yield the α-cyano-4-fluoro-3-phenoxybenzyl ester of 4-fluoro-3-phenoxybenzyl ester of 4-(4-chlorophenyl)-2-isopropyl-3-butenoic acid.

EXAMPLE 5

Each of the acids under column I is reacted with α-cyano-4-fluoro-3-phenoxybenzyl alcohol to yield the ester under column II.

I 4-chloro-2-isopropyl-4-phenyl-3-butenoic acid
2-isopropyl-3-methyl-4-phenyl-3-butenoic acid
4-(2-chlorophenyl)-2-isopropyl-3-butenoic acid
2-isopropyl-4-(4-methoxyphenyl)-3-butenoic acid
2-isopropyl-4-(4-methylphenyl)-3-butenoic acid
2-isopropyl-4-phenyl-3-butenoic acid
2-isopropyl-4-(pentafluorophenyl)-3-butenoic acid

II

α-cyano-4-fluoro-3-phenoxybenzyl 4-chloro-2-isopropyl-4-phenyl-3-butenoate
α-cyano-4-fluoro-3-phenoxybenzyl 2-isopropyl-3-methyl-4-phenyl-3-butenoate
α-cyano-4-fluoro-3-phenoxybenzyl 4-(2-chlorophenyl)-2-isopropyl-3-butenoate
α-cyano-4-fluoro-3-phenoxybenzyl 2-isopropyl-4-(4-methoxyphenyl)-3-butenoate
α-cyano-4-fluoro-3-phenoxybenzyl-2-isopropyl-4-(4-methylphenyl)-3-butenoate
α-cyano-4-fluoro-3-phenoxybenzyl 2-isopropyl-4-phenyl-3-butenoate
α-cyano-4-fluoro-3-phenoxybenzyl-2-isopropyl-4-(pentafluorophenyl)-3-butenoate

EXAMPLE 6

Each of the alcohols, 2-fluoro-5-phenoxybenzyl alcohol, 4-fluoro-3-(4-fluorophenoxy) benzyl alcohol, 2-fluoro-5-(4-fluorophenoxy) benzyl alcohol, 3-fluoro-5-phenoxybenzyl alcohol and 4-fluoro-3-(4-methylphenoxy)benzyl alcohol is reacted with 4-(4-fluorophenyl)-2-isopropyl-3-butenoic acid to yield the respective ester under column III.

III 2-fluoro-5-phenoxybenzyl 4-(4-fluorophenyl)-2-isopropyl-3-butenoate
4-fluoro-3-(4-fluorophenoxy)benzyl 4-(4-fluorophenyl)-2-isopropyl-3-butenoate
2-fluoro-5-(4-fluorophenoxy) benzyl 4-(4-fluorophenyl)-2-isopropyl-3-butenoate
3-fluoro-5-phenoxybenzyl 4-(4-fluorophenyl)-2-isopropyl-3-butenoate
4-fluoro-3-(4-methylphenoxy) benzyl 4-(4-fluorophenyl)-2-isopropyl-3-butenoate

EXAMPLE 7

Each of the acids under column IV is reacted with α-cyano-4-fluoro-3-phenoxybenzyl alcohol to yield the respective ester under column V.

IV 2-isopropyl-4-(4-trifluoromethylphenyl)-3-butenoic acid
2-isopropyl-4-(2-trifluoromethylphenyl)-3-butenoic acid
4-(2,4-difluorophenyl)-2-isopropyl-3-butenoic acid
4-(2-fluoro-4-trifluoromethylphenyl)-2-isopropyl-3-butenoic acid

V

α-cyano-4-fluoro-3-phenoxybenzyl 2-isopropyl-4-(4-trifluoromethylphenyl)-3-butenoate p1 α-cyano-4-fluoro-3-phenoxybenzyl 2-isopropyl-4-(2-trifluoromethylphenyl)-3-butenoate
α-cyano-4-fluoro-3-phenoxybenzyl 4-(2,4-difluorophenyl)-2-isopropyl-3-butenoate
α-cyano-4-fluoro-3-phenoxybenzyl 4-(2-fluoro-4-trifluoromethylphenyl)-2-isopropyl-3-butenoate

EXAMPLE 8

Each of α-ethynyl-4-fluoro-3-phenoxybenzyl alcohol and 4-fluoro-α-methyl-3-phenoxybenzyl alcohol is reacted with 4-(4-fluorophenyl)-2-isopropyl-3-butenoic acid to yield α-ethynyl-4-fluoro-3-phenoxybenzyl 4-(4-fluorophenyl)-2-isopropyl-3-butenoate and 4-fluoro-α-methyl-3-phenoxybenzyl 4-(4-fluorophenyl)-2-isopropyl-3-butenoate.

What is claimed is:

1. A compound of the following formula (A):

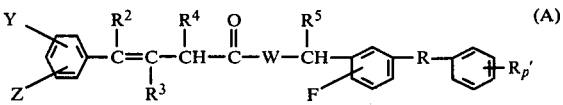

wherein:

R is oxygen, sulfur, methylene or carbonyl;
R' is hydrogen, fluoro, bromo, chloro, trifluoromethyl, methyl, methoxy or methylthio;
each of $R^2$ and $R^3$ is independently selected from hydrogen, chloro, fluoro, bromo, lower alkyl, lower alkenyl, lower alkoxy, cycloalkalkyl, and lower haloalkyl;
$R^4$ is lower alkyl of 2 to 5 carbon atoms, lower alkenyl of 2 to 5 carbon atoms, or cyano;
$R^5$ is hydrogen, cyano, ethynyl or methyl;
W is oxygen or sulfur;
t is zero, one, two, three or four;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio; and
Z is independently selected from the values of Y, cycloalkyl, and lower haloalkoxy; or
Y and Z form a methylenedioxy group.

2. A compound according to claim 1 wherein each of W and R is oxygen, p is zero or one, $R^4$ is isopropyl and each of $R^2$ and $R^3$ is hydrogen, fluoro, chloro or methyl.

3. A compound according to claim 2 wherein Y is hydrogen, bromo, chloro, fluoro, lower alkyl of 1 to 4 carbon atoms, trifluoromethyl, methoxy, ethoxy or methylthio and Z is hydrogen or independently selected from the values of Y.

4. A compound according to claim 3 wherein Z is hydrogen and t is zero or one.

5. A compound according to claim 4 wherein each of $R^2$ and $R^3$ is hydrogen, Y is in the para position, and $R^5$ is hydrogen or cyano.

6. A compound according to claim 3 of the formula:

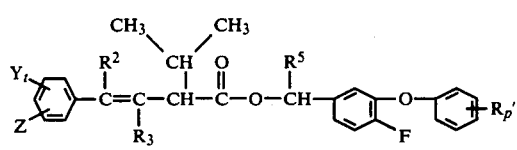

7. A compound according to claim 6 wherein Z is hydrogen and t is zero or one.

8. A compound according to claim 7 wherein each of $R^2$ and $R^3$ is hydrogen and p is zero or one, provided that when p is one, then R' is in the para position.

9. A compound according to claim 8 wherein Y is in the para position.

10. A compound according to claim 9 wherein $R^5$ is hydrogen or cyano.

11. A compound according to claim 10 wherein p is zero.

12. A compound according to claim 11 wherein Y is fluoro.

13. The compound, α-cyano-4-fluoro-3-phenoxybenzyl 4-(4-fluorophenyl)-2-isopropyl-3-butenoate, according to claim 12.

14. A compound according to claim 3 of the following formula:

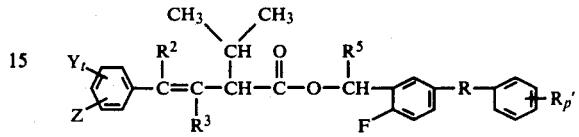

15. A compound according to claim 14 wherein each of $R^2$ and $R^3$ is hydrogen, t is zero or one, and p is zero or one, provided that when p is one, then R' is in the para position.

16. A compound according to claim 15 wherein Z is hydrogen and Y is in the para position.

17. A compound according to claim 16 wherein $R^5$ is hydrogen or cyano.

18. A compound according to claim 17 wherein p is zero.

* * * * *